(12) United States Patent
Meng et al.

(10) Patent No.: US 12,362,044 B2
(45) Date of Patent: Jul. 15, 2025

(54) METHOD FOR PREDICTING RETENTION TIME OF LIQUID CHROMATOGRAPHY UNDER DIFFERENT CHROMATOGRAPHIC CONDITIONS

(71) Applicant: Wuhan Zhihua Technology Co., Ltd., Wuhan (CN)

(72) Inventors: Chao Meng, Wuhan (CN); Hongbin Yang, Wuhan (CN); Ning Xia, Wuhan (CN)

(73) Assignee: Wuhan Zhihua Technology Co., Ltd., Wuhan (CN)

( * ) Notice: Subject to any disclaimer, the term of this patent is extended or adjusted under 35 U.S.C. 154(b) by 0 days.

(21) Appl. No.: 18/967,636

(22) Filed: Dec. 3, 2024

(65) Prior Publication Data

US 2025/0095794 A1 Mar. 20, 2025

(30) Foreign Application Priority Data

May 28, 2024 (CN) .......................... 202410669574.1

(51) Int. Cl.
  *G16C 20/30* (2019.01)
  *G16C 20/20* (2019.01)
  *G16C 20/70* (2019.01)
  *G16C 20/90* (2019.01)

(52) U.S. Cl.
  CPC ............ *G16C 20/30* (2019.02); *G16C 20/20* (2019.02); *G16C 20/70* (2019.02); *G16C 20/90* (2019.02)

(58) Field of Classification Search
  CPC ........ G16C 20/30; G16C 20/50; G16C 20/70; G16C 20/90
  See application file for complete search history.

(56) References Cited

U.S. PATENT DOCUMENTS

| 11,610,139 | B2* | 3/2023 | Bucher ................ G06N 3/0442 |
| 2004/0034477 | A1* | 2/2004 | McBrien ............ G01N 30/8693 702/22 |
| 2023/0045690 | A1 | 2/2023 | Sakhinana |
| 2024/0021277 | A1* | 1/2024 | Zaw ....................... G16C 20/70 |

FOREIGN PATENT DOCUMENTS

| CN | 116106461 B | 2/2024 |
| CN | 118243842 B | 8/2024 |
| WO | 2024089143 A | 5/2024 |

* cited by examiner

*Primary Examiner* — Lam S Nguyen (57) ABSTRACT

A method for predicting a retention time of liquid chromatography under different chromatographic conditions includes: collecting experimental data; extracting structural information of a molecule according to SMLIES information of a compound, and constructing a molecular graph structure based on the structural information of the molecule; obtaining a physicochemical property of the molecule in the compound, and quantifying the physicochemical property to obtain a physicochemical property description vector; obtaining chromatographic column data, and generating a chromatographic encoding vector based on this data; constructing a graph neural network model, including a graph network layer, a readout layer and a linear layer; utilizing a dataset to iteratively train the graph neural network model to obtain a trained graph neural network model; and obtaining the SMLIES information and chromatographic conditions of the compound to be predicted, inputting them into the trained graph neural network model, and outputting the predicted retention time result.

5 Claims, 3 Drawing Sheets

METHOD FOR PREDICTING RETENTION TIME OF LIQUID CHROMATOGRAPHY UNDER DIFFERENT CHROMATOGRAPHIC CONDITIONS

TECHNICAL FIELD

The present disclosure relates to the technical field of chromatography applications, in particular to a method for predicting a retention time of liquid chromatography under different chromatographic conditions.

BACKGROUND

A retention time measures a process of equilibrating a sample between a mobile phase and a stationary phase in liquid chromatography. Liquid chromatography is a complex physicochemical process that includes an ionization equilibrium of compounds in the mobile phase, a multiphase partition equilibrium, an adsorption-desorption equilibrium with a chromatographic column, etc. These processes depend on properties of the compounds themselves under the same experimental conditions, so predicting the retention time is equivalent to quantifying the properties of the corresponding compounds. With respect to types of the properties of the compounds, current methods for predicting the retention time may be divided into the following types.

1. Based on a mapping relationship between different chromatographic systems:

this type of method establishes a mapping relationship of the same compound under various chromatographic systems based on data synthesizing various chromatography, wherein a more representative one is PredRet. PredRet allows a user to upload data to expand a predictable chemical space and improve prediction precision. This type of method does not require any data other than a name of the compound, and predicts retention times in different chromatographic systems only through a mapping relationship of retention times of the compound that is shared between databases.

2. Based on a regression analysis of physicochemical properties:

this type of method extracts the physicochemical properties of a compound and uses a regression analysis to obtain a relationship between a retention time of liquid chromatography and these properties. A current study has given influences of parameters such as log D, an atomic charge, a rotatable chemical bond, and a hydrogen bond on the retention time, and found that log D has a greatest correlation. This type of method taps into the properties of the compound itself, so a model has certain scalability.

3. Based on chemoinformatics+machine learning:

This type of method is mainly based on molecular topology or three-dimensional structural information, and utilizes a molecular fingerprint generated by chemoinformatics with a machine learning method to predict a retention time. It first generates the molecular fingerprint according to the molecular topology information, and takes the molecular fingerprint as a description quantity to fit data using a machine learning or conventional linear regression method. This type of method is based on a principle that a chemical structure determines the properties, through a structural description of a molecule, the property of retention time is disassembled into contributions of individual substructures, and meanwhile the machine learning method relies on a large quantity of data to refine classification and regression of the substructures.

In existing technical solutions, only a fixed retention time can be given, but this is not consistent with the experience of daily experiments, in daily experiments, there are often different chromatographic columns and mobile phases, and only giving one retention time is obviously inconsistent with a real scenario, and cannot bring practical reference significance to an experimenter in the real analytical experiments of the reagent experimenter.

SUMMARY

In view of this, the present disclosure provides a method for predicting a retention time of liquid chromatography under different chromatographic conditions, predicting the retention time of the liquid chromatography based on a molecular fingerprint, a molecular descriptor, and chromatographic system information to improve accuracy.

A technical objective of the present disclosure is achieved as follows.

The present disclosure provides a method for predicting a retention time of liquid chromatography under different chromatographic conditions, including the following steps:

S1: collecting and cleaning experimental data which include SMLIES information of a compound, the chromatographic conditions, and corresponding retention time values, wherein the chromatographic conditions include chromatographic column information, a mobile phase condition, and a running time of a mobile phase;

S2: extracting structural information of a molecule according to the SMLIES information of the compound, and constructing a molecular graph structure based on the structural information of the molecule, wherein the molecular graph structure includes node characteristics, side characteristics, and an adjacency matrix;

S3: obtaining a physicochemical property of the molecule in the compound, and quantifying the physicochemical property to obtain a physicochemical property description vector;

S4: obtaining chromatographic column data, establishing a chromatographic column characteristic database based on the chromatographic column data, and encoding the chromatographic conditions of the compound based on the chromatographic column characteristic database to obtain a chromatographic encoding vector;

S5: constructing a graph neural network model, including a graph network layer, a readout layer and a linear layer;

S6: integrating the molecular graph structure, the physicochemical property description vector, the chromatographic encoding vector, and the retention time values of the experimental data into a dataset, and utilizing the dataset to iteratively train the graph neural network model until a loss function converges to obtain a trained graph neural network model; and S7: obtaining the SMLIES information and chromatographic conditions of the compound to be predicted, inputting them into the trained graph neural network model, and outputting and obtaining a retention time predicted result.

Based on the above solution, preferably, step S4 includes:

S41: collecting the chromatographic column data which includes different chromatographic columns and corresponding chromatographic column parameters, and binding and indexing each chromatographic column with the chromatographic column parameter thereof to establish the chromatographic column characteristic database;

S42: obtaining the chromatographic column used in an experiment according to the chromatographic column information in the experimental data, and utilizing the chromatographic column to search in the chromatographic column characteristic database to obtain a target chromatographic column parameter $C_1$;

S43: extracting a detection start time $t_1$ and a detection end time $t_2$ according to the running time of the mobile phase in the experimental data, and obtaining a mobile phase gradient $L_1$ at the detection start time $t_1$ and a mobile phase gradient $L_2$ at the detection end time $t_2$ in combination with the mobile phase condition; and S44: encoding the target chromatographic column parameter $C_1$, the detection start time $t_1$, the detection end time $t_2$, the mobile phase gradient $L_1$ at the detection start time $t_1$, and the mobile phase gradient $L_2$ at the detection end time $t_2$ to obtain chromatographic encoding vectors $[C_1, L_1, L_2, t_1, t_2]$.

Based on the above solution, preferably, in step S2, the node characteristics include an atom type, aromaticity, a heteroatom or not, in a ring or not, the number of hydrogen atoms, and the number of radical electrons; the side characteristics include a bond type, conjugate or not, on a ring or not, and a rotatable bond or not; and the adjacency matrix is constructed according to a molecular chemical bond of the compound, which is used to represent atoms, chemical bonds and a connection relationship thereof.

Based on the above solution, preferably, step S6 includes:

S61: dividing the dataset into a training set, a verification set, and a test set, wherein each training datum in the dataset contains a molecular graph structure, a physicochemical property description vector, a chromatographic encoding vector, and a retention time value;

S62: utilizing the training set to iteratively train the graph neural network, calculating a value of the loss function according to a difference between an output predicted retention time and retention time data, feeding back and adjusting parameters of the graph neural network model according to the value of the loss function until the loss function converges to a stable value, and obtaining the initially trained graph neural network model;

S63: utilizing the verification set to verify the initially trained graph neural network model, performing hyperparameter tuning for the initially trained graph neural network model on the verification set, and obtaining the verified graph neural network model; and S64: utilizing the test set to perform a model evaluation on the verified graph neural network model, finely tuning the verified graph neural network model according to an evaluation result, and obtaining the final trained graph neural network model.

Based on the above solution, preferably, in utilizing the dataset to iteratively train the graph neural network model, a training process of the graph neural network model with an individual training datum is as follows:

inputting the molecular graph structure into the graph network layer, identifying the atoms, the chemical bonds and the connection relationship thereof in the molecular graph structure according to the adjacency matrix, taking the atoms as nodes, performing an information transfer for the nodes to update node information, aggregating updated node information through an activation function, and outputting and obtaining node information data;

inputting the node information data, the physicochemical property description vector, and the chromatographic encoding vector into the readout layer to perform merging and encoding, and outputting and obtaining encoded data; and inputting the encoded data into linear layers, mapping the encoded data to a low dimensional space through a mapping function, extracting a target characteristic related to the retention time in the low dimensional space, and projecting the target characteristic to a scalar value to obtain the predicted retention time, wherein there are two linear layers, and a linear rectification function is set between the two linear layers.

Based on the above solution, preferably, a formula for the information transfer is expressed as follows:

$$V_i^{(t+1)} = \sigma\left(V_i^{(t)} + \sum_{j \in N(i)} h_{ij}^{(t)}\right);$$

In the formula, i represents a target node, j represents a source node, N(i) represents all source nodes from which the target node i receives the information transfer during an information transfer process, t and t+1 represent a $t^{th}$ transfer and a $(t+1)^{th}$ transfer, $$V_i^{(t+1)}$$

is node information of the target node i after a $(t+1)^{th}$ update, $V_i(t)$ is node information of the target node i after a $t^{th}$ update, σ is a sigmoid function, and $h_{ij}^{(t)}$ represents a sum of information of the source node j and side information between the source node j and the target node i.

Based on the above solution, preferably, a formula for aggregating the updated node information through the activation function is expressed as follows:

$$y_{molecul} = \Sigma_i V_i^{(t)};$$

wherein $y_{molecule}$ represents the node information data.

Based on the above solution, preferably, a formula for the encoded data is expressed as follows:

$$e_i = \text{concat}(c, m, l) * w + b;$$

In the formula, $e_i$ represents the encoded data, c represents the physicochemical property description vector, m represents a projection vector of the node information data after a projection, l represents the chromatographic encoding vector, w is a parameter weight learned by the graph neural network model, and b is a bias term.

Based on the above solution, preferably, the chromatographic column parameters include 7 parameters, which are: chromatographic column hydrophobicity, spatial selectivity, column hydrogen bond acidity, column hydrogen bond alkalinity, a chromatographic column ion exchange capacity at ph2.8, a chromatographic column ion exchange capacity at ph7.0, and a chromatographic column type respectively.

Based on the above solution, preferably, physicochemical properties of the molecule in the compound contain 17 physicochemical properties, which are: the number of hydrogen bond donors, the number of hydrogen bond acceptors, a polar surface area, an average number of hydrogen bonds on a surface, log P, a topological molecule polar surface area, a molecular weight, a molar refractive index, the number of rotatable chemical bonds, the number of aromatic rings, the number of aliphatic rings, the number of saturated aliphatic rings, a proportion of sp3 hybridized carbon atoms, a Chi0 index, a Chi4n index, a Kappa1 index, and a Kappa2 index respectively.

Compared with the prior art, the method of the present disclosure has the following beneficial effects.

(1) The present disclosure combines the physicochemical properties of a compound structure and processed description quantities of various mobile phase systems together as an input to machine learning. Wherein more critical chromatographic system information, which is based on encoding of the mobile phase and the gradients, can more comprehensively describe that the compound structure is influenced by various chromatographic systems. A deep learning part ensures accuracy and interpretability of the model through the GNN at the same time, and this mode can obtain most complete chemical structure characteristic information and the chromatographic system information during a retention time analysis of the compound, as well as the interpretable and scalable model.

(2) The present disclosure comprehensively considers molecular structure characteristics of the compound and influencing factors of the chromatographic conditions by constructing the molecular graph structure and extracting the physicochemical property description vector and the chromatographic encoding vector of the molecule, which makes the prediction of the retention time more accurate and comprehensive.

(3) The present disclosure adopts a graph neural network model, can effectively process structural information of molecules, makes full use of the correlation between the molecules and local characteristics, and improve a modeling ability for a complex molecular system, thus improving the accuracy of prediction of the retention time.

(4) The present disclosure establishes the chromatographic column characteristic database to encode the chromatographic column parameters with the chromatographic conditions of the compound, which helps to better capture the influence of different chromatographic conditions on the retention time, and improves a generalization ability and prediction accuracy of the model.

(5) In the molecular graph structure of the present disclosure, designs of the node characteristics and the side characteristics take into account a number of aspects, such as the atom type, the bond type, the aromaticity, etc., and these meticulous descriptions help to more accurately characterize the structural characteristics of the molecule, and improve understanding and processing ability of the model for the molecular information.

BRIEF DESCRIPTION OF DRAWINGS

To describe the technical solutions in the embodiments of the present invention or in the related art more clearly, the following briefly introduces the accompanying drawings for describing the embodiments or the related art. Apparently, the accompanying drawings in the following description show merely some embodiments of the present invention, and a person of ordinary skill in the art may still derive other drawings from the accompanying drawings without creative efforts.

DETAILED DESCRIPTION

The technical solutions in the embodiments of the present invention will be clearly and completely described below with reference to the embodiments of the present invention, and it is obvious that the described embodiments are only a part of the embodiments of the present invention but not all of them. All other embodiments obtained by a person of ordinary skill in the art based on the embodiments of present disclosure without making creative efforts shall fall within the protection scope of present disclosure.

Explanations of some of terms involved in the present disclosure:

Simplified Molecular Input Line Entry Specification (SMILES): a simplified molecular input line entry specification is a specification that explicitly describes a structure of a molecule in ASCII strings.

SMiles ARbitrary Target Specification (SMARTS): it is a language for describing a pattern and an attribute of a molecule.

Retention Time: a time elapsed in chromatography from a beginning of an injection of a separated sample component to a time when a maximum concentration of the component appears after a chromatographic column.

Mobile phase: a substance that carries a component to move forward during a chromatography process.

Stationary phase: it is a substance that separates components during a chromatographic process, and refers specifically to a chromatographic column herein.

Protonation: a process by which a compound molecule absorbs a positive hydrogen ion.

Deprotonation: a process by which a compound molecule loses a positive hydrogen ion.

pH: a negative logarithm of a concentration of hydrogen ions in a solution and used to quantitatively measure a degree of acidity. It refers specifically to being in an aqueous solution in the present disclosure.

log D: a grease distribution coefficient for a compound in a multi-ionization form considering ionization.

log P: a grease distribution coefficient for a compound in a non-ionization form.

Morgan Fingerprint: a topological molecular fingerprint.

GNN: a graph neural network is an artificial neural network model for processing graph data.

RDKit: open source chemical informatics software.

Figure 1:
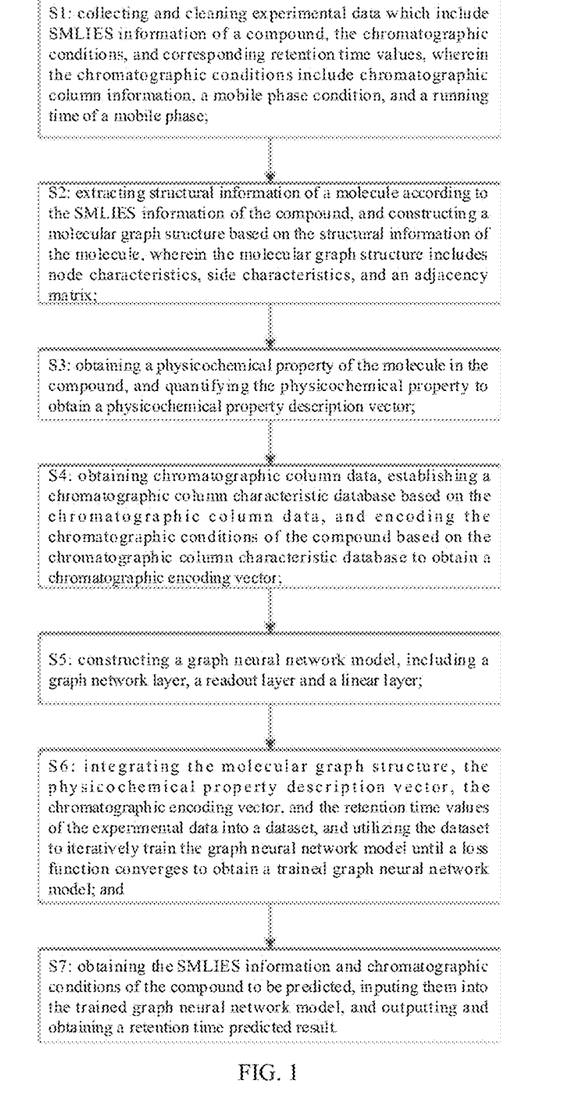
FIG. 1 is a flowchart of a method of an embodiment of the present disclosure.

As shown in FIG. 1, the present disclosure provides a method for predicting a retention time of liquid chromatography under different chromatographic conditions, including the following steps:

S1: collecting and cleaning experimental data which include SMLIES information of a compound, the chromatographic conditions, and corresponding retention time values, wherein the chromatographic conditions include chromatographic column information, a mobile phase condition, and a running time of a mobile phase;

S2: extracting structural information of a molecule according to the SMLIES information of the compound, and constructing a molecular graph structure based on the structural information of the molecule, wherein the molecular graph structure includes node characteristics, side characteristics, and an adjacency matrix;

S3: obtaining a physicochemical property of the molecule in the compound, and quantifying the physicochemical property to obtain a physicochemical property description vector;

S4: obtaining chromatographic column data, establishing a chromatographic column characteristic database based on the chromatographic column data, and encoding the chromatographic conditions of the compound based on the chromatographic column characteristic database to obtain a chromatographic encoding vector;

S5: constructing a graph neural network model, including a graph network layer, a readout layer and a linear layer;

S6: integrating the molecular graph structure, the physicochemical property description vector, the chromatographic encoding vector, and the retention time values of the experimental data into a dataset, and utilizing the dataset to iteratively train the graph neural network model until a loss function converges to obtain a trained graph neural network model; and S7: obtaining the SMLIES information and chromatographic conditions of the compound to be predicted, inputting them into the trained graph neural network model, and outputting and obtaining a retention time predicted result.

Specifically, in an embodiment of the present disclosure, step S1 includes:

collecting experimental data which are derived from artificial experimental data generated in an experimental environment, and include SMLIES information of a compound, the chromatographic conditions, and corresponding retention time values.

In this embodiment, a total of 67594 data are obtained, containing the retention time values of 67594 organic compounds under 9 mobile phase systems. After the data are collected in a uniform manner, the compound and mobile phase data are cleaned, and compounds therein that do not produce liquid phase peaks are removed so as to obtain complete outlier-free data. Specifically, a data processing tool may be used to clean the experimental data in a specific process that includes:

All compound data showing liquid phase peaks are screened according to experimental requirements and cleaning criteria, and these data are complete and do not contain outliers.

Outlier detection is performed on the retention time data using a statistical method, such as an outlier detection algorithm, or a visualization tool, such as a box plot, to identify an outlier.

The detected outlier is processed by deleting the outlier or performing a data correction such as replacing it with a mean, a median, etc.

Whether there are duplicate data records checked, and if there are duplicate data, a de-duplication operation is performed to ensure that each sample in the dataset is unique.

Whether there is a missing value in the dataset is checked, and for processing of the missing value, a choice is to delete a sample containing the missing value or to fill it, such as mean, median, and mode filling.

The cleaned experimental data are integrated into a complete dataset, ensuring that each sample contains an organic compound, a mobile phase system, and corresponding retention time data.

Specifically, in an embodiment of the present disclosure, step S2 includes the following.

RDKit is used to parse a SMILES string of the compound, structural information of a molecule is extracted, and a molecular graph structure is constructed based on the information, wherein the molecular graph structure includes node characteristics, side characteristics, and an adjacency matrix.

The node characteristics include:

an atom type: the atom type is determined according to an element type (C, H, O, etc.) of each atom in the molecule;

aromaticity: whether an atom belongs to an aromatic ring may be determined according to bonds around the atom;

a heteroatom or not: whether the atom is a heteroatom (not carbon, hydrogen, oxygen, nitrogen, etc.) may be determined according to the element type;

in a ring or not: whether the atom is located in a ring may be determined by a ring detection algorithm;

the number of hydrogen atoms: the number of the hydrogen atoms connected around each atom is counted; and the number of radical electrons: the number of unpaired electrons around the atom is calculated and used to describe an electronic structure of the atom.

The side characteristics include:

a bond type, the side characteristics are determined according to the type (single, double, triple, etc.) of a chemical bond between atoms;

conjugate or not: whether the bond between two atoms is a conjugate bond is judged;

on a ring or not, whether the bond connecting the two atoms is on a ring is judged; and a rotatable bond or not: whether the bond connecting the two atoms is a rotatable bond is judged.

An adjacency matrix is constructed according to the molecular chemical bonds of the compound, and each element of the matrix represents a connection relationship between two atoms. The adjacency matrix is used to represent atoms, chemical bonds and the connection relationship thereof.

COO is used as an example for illustration.

First, the SMILES string 'CCO' is converted to a molecular object mol in RDKit via a Chem.MolFromSmiles(smiles) method.

The number of atoms in the molecule is obtained via mol.GetNumAtoms( ) and stored in a num_atoms variable.

Each atom in the molecule is traversed using mol.GetAtoms( ) and following operations are performed on each atom:

the element type of the atom is obtained using atom.GetSymbol( ) and stored in an atom_type variable.

The number of hydrogen atoms around the atom is obtained using atom.GetTotalNumHs( ) and stored in a num_hydrogens variable.

The element type and number of hydrogen atoms for each atom are output.

The connection relationship (adjacency matrix) of the molecule is obtained:

the adjacency matrix of the molecule is obtained using a Chem.GetAdjacencyMatrix(mol) method, which represents the connection relationship between atoms.

The adjacency matrix is stored in an adj_matrix variable.

Finally, the adjacency matrix is output, showing the connection relationship between atoms in the molecule.

Specifically, in an embodiment of the present disclosure, step S2 includes the following.

obtaining physicochemical properties of the molecule, using 17 physicochemical property description quantities containing the number of hydrogen bond donors, the number of hydrogen bond acceptors, a polar surface area, an average number of hydrogen bonds on a surface, log P, a topological molecule polar surface area, a molecular weight, a molar refractive index, the number of rotatable chemical bonds, the number of aromatic rings, the number of aliphatic rings, the number of saturated aliphatic rings, a proportion of sp3 hybridized carbon atoms, a Chi index, a Chi4n index, a Kappa1 index, and a Kappa2 index.

In this embodiment, the RDKit tool may still be used to calculate the physicochemical properties of the molecule, and after the 17 physicochemical property description quantities are obtained, they are quantified to form a 17-dimensional physicochemical property description vector.

As an example, benzaldehyde, whose chemical formula is $C_7H_6O$, is an organic compound with an aromatic ring structure.

First, 17 physicochemical property description quantities of a benzaldehyde molecule are calculated:

By analyzing positions of hydrogen atoms and oxygen-containing functional groups in the benzaldehyde, the number of hydrogen bond donors is calculated to be 0, and the number of hydrogen bond acceptors is calculated to be 1.

The polar surface area is obtained by calculating a surface area and an average number of hydrogen bonds of a polar portion in the benzaldehyde molecule, and the calculated polar surface area is 47.96 $Å^2$, and the average number of hydrogen bonds on the surface is 0.

Lipophilicity of benzaldehyde is described by calculating its log P value, which is 1.5.

The topological molecule polar surface area is obtained by calculating the number of polar atoms (e.g., oxygen atoms) in the benzaldehyde molecule, which is calculated to be 17.07 $Å^2$.

The molecular weight is a sum of relative atomic masses of all atoms in the benzaldehyde molecule, and the molecular weight of benzaldehyde is 106.04 g/mol.

The molar refractive index is a physicochemical property that indicates an ability of a substance to refract light. The molar refractive index is represented by a symbol RM and is defined as:

$$R_M = \frac{(n^2 - 1)}{\rho},$$

n is a refractive index of the substance, and $\rho$ is a density of the substance. The molar refractive index of benzaldehyde is calculated to be 31.83.

The number of freely rotatable chemical bonds in benzaldehyde is calculated to be 1.

Benzaldehyde has an aromatic ring and no aliphatic ring or saturated aliphatic ring, so the number of aromatic rings is 1, and the number of aliphatic rings and the number of saturated aliphatic rings are 0.

The proportion of sp3 hybridized carbon atoms to all carbon atoms in benzaldehyde is calculated; and there are no sp3 hybridized carbon atoms in benzaldehyde, so the proportion is 0.

The Chi0 index represents a sum of connectivity and non-connectivity measures of all atoms in the molecule. For the benzaldehyde molecule, the Chi0 index is obtained by calculating connectivity and non-connectivity of the atoms in its topological structure, and its value is calculated to be 5.82.

The Chi4n index represents a sum of fourth-order connectivity and nonconnectivity measures of all atoms in the molecule. The Chi4n index is obtained by calculating fourth-order connectivity and non-connectivity of the atoms in the benzaldehyde molecule, and its value is calculated to be 0.53.

The Kappa1 index and Kappa2 index are used to measure a degree of branching of the molecule and the number of rings. The Kappa1 index represents the degree of branching of the molecule, and The Kappa2 index represents the number of rings in the molecule. The Kappa1 index and Kappa2 index are obtained by calculating the number of branches and rings in the topological structure of the benzaldehyde molecule, and their values are calculated to be 5.04 and 2.26.

In summary, the physicochemical property description vector may be quantified as P=(0, 1, 47.96, 0.0, 1.5, 17.07, 106.04, 31.83, 1, 1, 0, 0, 0.0, 5.82, 0.53, 5.04, 2.26).

Specifically, in an embodiment of the present disclosure, step S4 includes the following.

S41: collecting the chromatographic column data which includes different chromatographic columns and corresponding chromatographic column parameters, and binding and indexing each chromatographic column with the chromatographic column parameter thereof to establish the chromatographic column characteristic database;

S42: obtaining the chromatographic column used in an experiment according to the chromatographic column information in the experimental data, and utilizing the chromatographic column to search in the chromatographic column characteristic database to obtain a target chromatographic column parameter $C_1$;

S43: extracting a detection start time $t_1$ and a detection end time $t_2$ according to the running time of the mobile phase in the experimental data, and obtaining a mobile phase gradient $L_1$ at the detection start time $t_1$ and a mobile phase gradient $L_2$ at the detection end time $t_2$ in combination with the mobile phase condition; and S44: encoding the target chromatographic column parameter $C_1$, the detection start time $t_1$, the detection end time $t_2$, the mobile phase gradient $L_1$ at the detection start time $t_1$, and the mobile phase gradient $L_2$ at the detection end time $t_2$ to obtain chromatographic encoding vectors $[C_1, L_1, L_2, t_1, t_2]$.

In this embodiment, a public chromatographic column data PQRI Database is first collected to establish a chromatographic column characteristic database according to chromatographic column parameters. The chromatographic column parameters include 7 parameters, which are: chromatographic column hydrophobicity, spatial selectivity, column hydrogen bond acidity, column hydrogen bond alkalinity, a chromatographic column ion exchange capacity at ph2.8, a chromatographic column ion exchange capacity at ph7.0, and a chromatographic column type respectively. During quantification, the first 6 chromatographic column parameters are specific values, and the chromatographic column type is quantified using OneHot encoding. Afterwards, MySQL may be used to construct the chromatographic column characteristic database:

a data table is created for storing chromatographic column characteristic data, and the table should contain the following fields: chromatographic column name or identifier (as a primary bond or unique index), chromatographic column hydrophobicity, spatial selectivity, column hydrogen bond acidity, column hydrogen bond alkalinity, chromatographic column ion exchange capacity at ph2.8, chromatographic column ion exchange capacity at ph7.0, and chromatographic column type (quantified using One-Hot encoding). The collected chromatographic column data are inserted into the data table. When a chromatographic column name or identifier is input, the value is used as a query condition to search in the database. A corresponding chromatographic column record is quickly located through the index, and the relevant chromatographic column parameters are returned. Specifically, the chromatographic column name may be a trade name of a chromatographic column, and the identifier may be a model number or an internal number.

The chromatographic column used in an experiment is obtained according to the chromatographic column information of all samples in the experimental data, and the chromatographic column characteristic database is searched according to the chromatographic column name, model number or internal number to obtain target chromatographic column parameters $C_1$; There are 7 target chromatographic column parameters, which are represented in a form of 14-dimensional vectors, wherein the first 6 parameters are values, and the chromatographic column type is encoded as 8-dimensional encoding using OneHot encoding, thus the target chromatographic column parameters are 14-dimensional vectors.

A detection start time $t_1$ and a detection end time $t_2$ for each experiment are obtained according to the running time of the mobile phase in the experimental data, $t_1$ and $t_2$ are taken in minutes, a mobile phase gradient at $t_1$ is obtained and denoted as $L_1$, and a mobile phase gradient at $t_2$ is obtained and denoted as $L_2$, after which encoding is performed with $[C_1, L_1, L_2, t_1, t_2]$, i.e., the chromatographic encoding vector is obtained.

In a specific example, $t_1$ is set to be 0.2 min of the running time, and $t_2$ is 1.8 min of the running time, i.e., the liquid chromatography experiment starts detection from 0.2 min to 1.8 min, i.e., the end of detection. The mobile phase conditions used in the experiment are acetonitrile and water, the mobile phase gradient refers to a ratio of acetonitrile to water, the mobile phase condition is 0.05 at 0.2 min and 0.8 at 1.8 min, and then the chromatographic encoding vector is $[C_1, 0.05, 0.8, 0.2, 1.8]$.

Specifically, $t_1$ and $t_2$ may also serve as a range of values when the retention time is predicted.

After the above processing of the experimental data, each sample contains a molecular graph structure, a physicochemical property description vector, a chromatographic encoding vector, and a real retention time value, which is used as a basis for constructing the dataset used to train the model, and the dataset is divided into a training set, a verification set, and a test set.

Specifically, the graph neural network model includes a graph network layer, a readout layer and a linear layer. A process of training the graph neural network model using the dataset includes:
utilizing the training set to iteratively train the graph neural network, calculating a value of the loss function according to a difference between an output predicted retention time and retention time data, feeding back and adjusting parameters of the graph neural network model according to the value of the loss function until the loss function converges to a stable value, and obtaining the initially trained graph neural network model;
utilizing the verification set to verify the initially trained graph neural network model, performing hyper-parameter tuning for the initially trained graph neural network model on the verification set, and obtaining the verified graph neural network model; and
utilizing the test set to perform a model evaluation on the verified graph neural network model, finely tuning the verified graph neural network model according to an evaluation result, and obtaining the final trained graph neural network model.

In one embodiment, it may be that a portion of the data is first divided as the independent test set, the other portion of the data is used to divide the training set and the verification set, and a k-fold cross-verification manner is used to train the graph neural network model using different combinations of data subsets. The loss function used during training is an L1 loss function.

Specifically, in utilizing the dataset to iteratively train the graph neural network model, a training process of the graph neural network model with an individual training datum is as follows:
inputting the molecular graph structure into the graph network layer, identifying the atoms, the chemical bonds and the connection relationship thereof in the molecular graph structure according to the adjacency matrix, taking the atoms as nodes, performing an information transfer for the nodes to update node information, aggregating updated node information through an activation function, and outputting and obtaining node information data;
inputting the node information data, the physicochemical property description vector, and the chromatographic encoding vector into the readout layer to perform merging and encoding, and outputting and obtaining encoded data; and
inputting the encoded data into linear layers, mapping the encoded data to a low dimensional space through a mapping function, extracting a target characteristic related to the retention time in the low dimensional space, and projecting the target characteristic to a scalar value to obtain the predicted retention time, wherein there are two linear layers, and a linear rectification function is set between the two linear layers.

Figure 2:
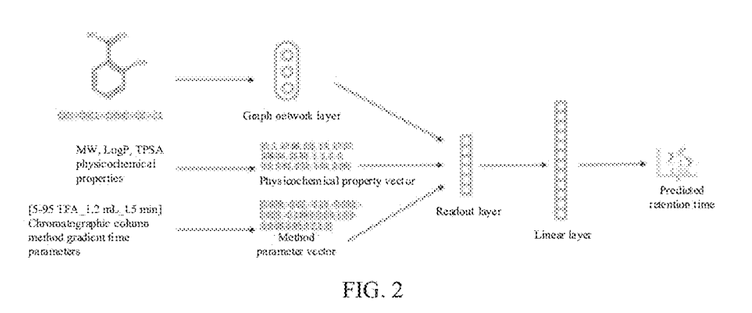
FIG. 2 is a flowchart of model processing of an embodiment of the present disclosure.

Referring to FIG. 2, in a specific example, a compound to be predicted is OC(=O)C1=C(O)C=CC=C1 with a structural formula shown in FIG. 2:

The graph neural network model may adopt a structural framework of a graph convolutional network, e.g., the graph network layers adopt a plurality of GCN structures, i.e., graph convolutional neural network structures, and in each graph network layer, a node receives information from neighboring nodes and updates node characteristics through an aggregation function. By stacking the plurality of graph network layers, higher-level node characteristic information may be gradually extracted and propagated.

The readout layer is used to merge and encode node information data, the physicochemical property description vector, and the chromatographic encoding vector. In this embodiment, after OC(=O)C1=C(O)C=CC=C1 is quantified and encoded, its physicochemical property description vector is [0, 1, 47.96, 0.0, 1.5, 17.07, 106.04, 31.83, 1, 1, 0, 0, 0.0, 5.82, 0.53, 5.04, 2.26], and its chromatographic encoding vector is [0.929, −0.02, −0.19, −0.033, −0.023, −0.139, 0, 0, 0, 0, 1, 0, 0, 0, 0.05, 0.95, 0.2, 1.3].

The graph structure as shown in FIG. 2 is input into the graph network layer to obtain the node information data, and then the node information data, the physicochemical property description vector, and the chromatographic encoding vector are input into the readout layer, and the readout layer adopts a multilayer perceptron (MLP) structure, including several fully connected layers and activation functions. After the input data (the node information data, the physicochemical property description vector, and the chromatographic encoding vector) are processed through the plurality of fully connected layers and activation functions, encoded data are obtained.

The linear layer contains two layers of linear transformations and a linear rectification function (ReLU) for mapping the encoded data to a low dimensional space and extracting a target characteristic related to the retention time. The first layer of linear transformation maps the input data to an intermediate characteristic space, and the activation function ReLU is used to introduce nonlinearity. The second layer of linear transformation maps an intermediate characteristic to the output layer, and the output layer is a scalar value, i.e., a predicted retention time.

In training the graph neural network model using the dataset, the molecular graph structure is first input into the graph network layer, and according to the adjacency matrix, the graph network layer identifies the atoms, chemical bonds, and the connection relationship between them in the molecular graph structure. Each atom is taken as a node to start the process of information transfer and node information update.

In the graph network layer, the node receives information from neighboring nodes and updates its own characteristic representation through an information transfer mechanism. A formula for the information transfer is expressed as follows:

$$V_i^{(t+1)} = \sigma\left(V_i^{(t)} + \sum_{j \in N(i)} h_{ij}^{(t)}\right);$$

in the formula, i represents a target node, j represents a source node, N(i) represents all source nodes from which the target node i receives the information transfer during an information transfer process, t and t+1 represent a $t^{th}$ transfer and a $(t+1)^{th}$ transfer, $$V_i^{(t+1)}$$

is node information of the target node i after a $(t+1)^{th}$ update, $V_i^{(t)}$ is node information of the target node i after a $t^{th}$ update, $\sigma$ is a sigmoid function, and $h_{ij}^{(t)}$ represents a sum of information of the source node j and side information between the source node j and the target node i;

Through a plurality of rounds of information transfers, the characteristics of the node are progressively updated and fused to capture richer local and global information. The updated node information is nonlinearly processed by the activation function, and then an aggregation operation is performed to obtain the node information data. A formula for aggregating the updated node information through the activation function is expressed as follows:

$$y_{molecule} = \sum_i V_i^{(t)};$$

wherein $y_{molecule}$ represents the node information data.

The obtained node information data, the physicochemical property description vector, and the chromatographic encoding vector are input into the readout layer. In the readout layer, the node information data, the physicochemical property description vector, and the chromatographic encoding vector are processed through the multilayer perceptron (MLP) structure. These characteristic data will be processed by the fully connected layer and activation function, and finally the encoded data are output, which contain information that synthesizes various characteristics. A formula for the encoded data is expressed as follows:

$$e_i = concat(c, m, l) * w + b;$$

In the formula, $e_i$ represents the encoded data, c represents the physicochemical property description vector, m represents a projection vector of the node information data after a projection, l represents the chromatographic encoding vector, w is a parameter weight learned by the graph neural network model, and b is a bias term.

The encoded data are fed into the linear layer, which are mapped to a low dimensional space by a mapping function. In the low dimensional space, the linear layer extracts the target characteristic related to the retention time. A nonlinear transformation is introduced between the two linear layers to better capture a complex relationship of the data through the processing of the two layers of linear transformations and the linear rectification function (ReLU). Finally, the extracted target characteristic is projected to the scalar value to obtain the predicted retention time.

It needs to be noted that the linear layer may map the high-dimensional encoding of the readout layer to the low dimensional space, extracting a key characteristic relevant to the prediction of retention time. ReLU is introduced between the two linear layers, allowing the model to learn the nonlinear relationship between input characteristics and the retention time. By reducing characteristic dimensions layer by layer and eventually projecting them to the scalar value (a retention time predicted value), the model learns a compact mapping function that maps high-dimensional molecular and chromatographic condition information to a value space of retention time. Therefore, a value of the predicted retention time can be obtained according to the encoding of the readout layer.

Figure 3:
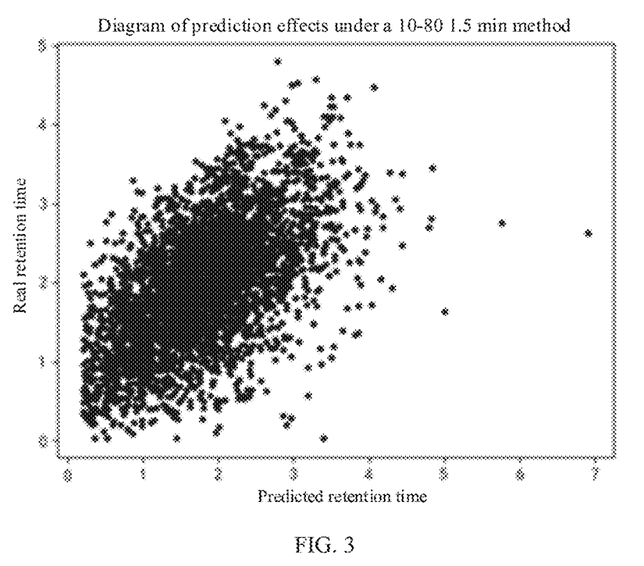
FIG. 3 is a diagram of a training effect of a graph neural network model of an embodiment of the present disclosure.

Specifically, please refer to FIG. 3, which is a diagram of a prediction effect of a graph neural network model on a dataset of the present disclosure, where a horizontal coordinate refers to a real retention time values in the dataset, and a vertical coordinate is a predicted retention time predicted by the model. As can be seen in FIG. 3, the method of the present disclosure can predict the retention time more accurately.

After the graph neural network model is trained, the SMLIES information and chromatographic conditions of the compound to be predicted are obtained, the molecular graph structure is constructed and vector encoding is performed by the method of the present disclosure to obtain the molecular graph structure, the physicochemical property description vector, and the chromatographic encoding vector, and the accurate predicted value of retention time may be obtained by inputting these data into the trained graph neural network model.

It needs to be noted that the present disclosure comprehensively considers molecular structure characteristics of the compound and influencing factors of the chromatographic conditions by constructing the molecular graph structure and extracting the physicochemical property description vector and the chromatographic encoding vector of the molecule, which may be adapted to a variety of different chromatographic gradients, and makes the prediction of the retention time more accurate and comprehensive.

It should be understood that the retention time obtained when the chemical structure is subjected to a chemical analysis is correlated with the chromatographic system, and different ways of encoding the chromatographic system or the use of different machine learning models may also realize the purpose of retention time prediction.

The above describes the preferred embodiments of the present invention and is not intended to limit the present invention. Any modification, equivalent replacement, and improvement made within the spirit and scope of the present invention shall fall within the protection scope of the present invention.

What is claimed is:

1. A method for predicting a retention time of liquid chromatography under different chromatographic conditions, comprising the following steps:
   S1: collecting and cleaning experimental data which include SMLIES information of a compound, the chromatographic conditions, and corresponding retention time values, wherein the chromatographic conditions include chromatographic column information, a mobile phase condition, and a running time of a mobile phase;
   S2: extracting structural information of a molecule according to the SMLIES information of the compound, and constructing a molecular graph structure based on the structural information of the molecule, wherein the molecular graph structure includes node characteristics, side characteristics, and an adjacency matrix;
   S3: obtaining a physicochemical property of the molecule in the compound, and quantifying the physicochemical property to obtain a physicochemical property description vector;
   S4: obtaining chromatographic column data, establishing a chromatographic column characteristic database based on the chromatographic column data, and encoding the chromatographic conditions of the compound based on the chromatographic column characteristic database to obtain a chromatographic encoding vector;
   S5: constructing a graph neural network model, comprising a graph network layer, a readout layer and a linear layer;
   S6: integrating the molecular graph structure, the physicochemical property description vector, the chromatographic encoding vector, and the retention time values of the experimental data into a dataset, and utilizing the dataset to iteratively train the graph neural network model until a loss function converges to obtain a trained graph neural network model; and
   S7: obtaining the SMLIES information and chromatographic conditions of the compound to be predicted, inputting them into the trained graph neural network model, and outputting and obtaining a retention time predicted result;
   wherein in step S2, the node characteristics comprise an atom type, aromaticity, a heteroatom or not, in a ring or not, the number of hydrogen atoms, and the number of radical electrons; the side characteristics include a bond type, conjugate or not, on a ring or not, and a rotatable bond or not; and the adjacency matrix is constructed according to a molecular chemical bond of the compound, which is used to represent atoms, chemical bonds and a connection relationship thereof;
   step S6 comprises:
   S61: dividing the dataset into a training set, a verification set, and a test set, wherein each training datum in the dataset contains a molecular graph structure, a physicochemical property description vector, a chromatographic encoding vector, and a retention time value;
   S62: utilizing the training set to iteratively train the graph neural network, calculating a value of the loss function according to a difference between an output predicted retention time and retention time data, feeding back and adjusting parameters of the graph neural network model according to the value of the loss function until the loss function converges to a stable value, and obtaining the initially trained graph neural network model;
   S63: utilizing the verification set to verify the initially trained graph neural network model, performing hyperparameter tuning for the initially trained graph neural network model on the verification set, and obtaining the verified graph neural network model; and
   S64: utilizing the test set to perform a model evaluation on the verified graph neural network model, finely tuning the verified graph neural network model according to an evaluation result, and obtaining the final trained graph neural network model;
   in utilizing the dataset to iteratively train the graph neural network model, a training process of the graph neural network model with an individual training datum is as follows:
   inputting the molecular graph structure into the graph network layer, identifying the atoms, the chemical bonds and the connection relationship thereof in the molecular graph structure according to the adjacency matrix, taking the atoms as nodes, performing an information transfer for the nodes to update node information, aggregating updated node information through an activation function, and outputting and obtaining node information data;
   inputting the node information data, the physicochemical property description vector, and the chromatographic encoding vector into the readout layer to perform merging and encoding, and outputting and obtaining encoded data; and
   inputting the encoded data into linear layers, mapping the encoded data to a low dimensional space through a mapping function, extracting a target characteristic related to the retention time in the low dimensional space, and projecting the target characteristic to a scalar value to obtain the predicted retention time, wherein there are two linear layers, and a linear rectification function is set between the two linear layers;
   A formula for the information transfer is expressed as follows:

$$V_i^{(t+1)} = \sigma\left(V_i^{(t)} + \sum_{j \in N(i)} h_{ij}^{(t)}\right);$$

in the formula, i represents a target node, j represents a source node, N(i) represents all source nodes from which the target node i receives the information transfer during an information transfer process, t and t+1 represent a $t^{th}$ transfer and a $(t+1)^{th}$ transfer, $V_i^{(t+1)}$ is node information of the target node i after a $(t+1)^{th}$ update, $V_i^{(t)}$ is node information of the target node i after a $t^{th}$ update, σ is a sigmoid function, and $h_{ij}^{(t)}$ represents a sum of information of the source node j and side information between the source node j and the target node i;

A formula for aggregating the updated node information through the activation function is expressed as follows:

$$y_{molecule} = \sum_i V_i^{(t)};$$

wherein $y_{molecule}$ represents the node information data.

2. The method for predicting the retention time of the liquid chromatography under the different chromatographic conditions according to claim 1, wherein step S4 comprises:

S41: collecting the chromatographic column data which include different chromatographic columns and corresponding chromatographic column parameters, and binding and indexing each chromatographic column with the chromatographic column parameter thereof to establish the chromatographic column characteristic database;

S42: obtaining the chromatographic column used in an experiment according to the chromatographic column information in the experimental data, and utilizing the chromatographic column to search in the chromatographic column characteristic database to obtain a target chromatographic column parameter $C_1$;

S43: extracting a detection start time $t_1$ and a detection end time $t_2$ according to the running time of the mobile phase in the experimental data, and obtaining a mobile phase gradient $L_1$ at the detection start time $t_1$ and a mobile phase gradient $L_2$ at the detection end time $t_2$ in combination with the mobile phase condition; and S44: encoding the target chromatographic column parameter $C_1$, the detection start time $t_1$, the detection end time $t_2$, the mobile phase gradient $L_1$ at the detection start time $t_1$, and the mobile phase gradient $L_2$ at the detection end time $t_2$ to obtain chromatographic encoding vectors $[C_1, L_1, L_2, t_1, t_2]$.

3. The method for predicting the retention time of the liquid chromatography under the different chromatographic conditions according to claim 1, wherein a formula for the encoded data is expressed as follows:

$$e_i = concat(c, m, l) * w + b;$$

In the formula, $e_i$ represents the encoded data, c represents the physicochemical property description vector, m represents a projection vector of the node information data after a projection, l represents the chromatographic encoding vector, w is a parameter weight learned by the graph neural network model, and b is a bias term.

4. The method for predicting the retention time of the liquid chromatography under the different chromatographic conditions according to claim 1, wherein the chromatographic column parameters comprise 7 parameters, which are: chromatographic column hydrophobicity, spatial selectivity, column hydrogen bond acidity, column hydrogen bond alkalinity, a chromatographic column ion exchange capacity at ph2.8, a chromatographic column ion exchange capacity at ph7.0, and a chromatographic column type respectively.

5. The method for predicting the retention time of the liquid chromatography under the different chromatographic conditions according to claim 1, wherein physicochemical properties of the molecule in the compound contain 17 physicochemical properties, which are: the number of hydrogen bond donors, the number of hydrogen bond acceptors, a polar surface area, an average number of hydrogen bonds on a surface, log P, a topological molecule polar surface area, a molecular weight, a molar refractive index, the number of rotatable chemical bonds, the number of aromatic rings, the number of aliphatic rings, the number of saturated aliphatic rings, a proportion of sp3 hybridized carbon atoms, a Chi0 index, a Chi4n index, a Kappa1 index, and a Kappa2 index respectively.

* * * * *